(12) United States Patent
Kim et al.

(10) Patent No.: US 11,400,267 B2
(45) Date of Patent: Aug. 2, 2022

(54) MICRONEEDLE PATCH, AND METHOD AND DEVICE FOR MANUFACTURING MICRONEEDLE

(71) Applicant: SAMSUNG ELECTRONICS CO., LTD., Suwon-si (KR)

(72) Inventors: Moo-rim Kim, Suwon-si (KR); Jeong-gun Lee, Seoul (KR); Shin-hee Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 606 days.

(21) Appl. No.: 16/345,617

(22) PCT Filed: Aug. 9, 2017

(86) PCT No.: PCT/KR2017/008591
§ 371 (c)(1),
(2) Date: Apr. 26, 2019

(87) PCT Pub. No.: WO2018/079990
PCT Pub. Date: May 3, 2018

(65) Prior Publication Data
US 2019/0269896 A1    Sep. 5, 2019

(30) Foreign Application Priority Data

Oct. 28, 2016    (KR) .................. 10-2016-0142099

(51) Int. Cl.
*A61M 37/00*    (2006.01)
*A61L 31/10*    (2006.01)
*A61L 31/14*    (2006.01)

(52) U.S. Cl.
CPC .......... *A61M 37/0015* (2013.01); *A61L 31/10* (2013.01); *A61M 37/00* (2013.01); *A61L 31/14* (2013.01); *A61M 2037/0023* (2013.01)

(58) Field of Classification Search
CPC .............. A61M 37/0015; A61M 37/00; A61M 2037/0023; A61M 2037/0046;
(Continued)

(56) References Cited

U.S. PATENT DOCUMENTS 6,050,988 A    4/2000 Zuck
8,236,368 B2   8/2012 Jung et al.
(Continued)

FOREIGN PATENT DOCUMENTS

CN    105727438 A    7/2016
JP    2005-537057 A   12/2005
(Continued)

OTHER PUBLICATIONS

International Searching Report dated Nov. 15, 2017 by the International Searching Authority in counterpart International Patent Application No. PCT/KR2017/008591. (PCT/ISA/210).
(Continued)

*Primary Examiner* — Amber R Stiles
(74) *Attorney, Agent, or Firm* — Sughrue Mion, PLLC

(57) ABSTRACT

According to various embodiments of the disclosure, a microneedle patch may include: microneedles including a viscous composition; an adhesive sheet adhered to the skin; and a base sheet having the microneedles arranged thereon, wherein the shape of the microneedles has a spirally-twisted screw shape so as to have a first incline facing a first direction and a second incline facing a second direction, which is the direction opposite to the first direction, and the diameter of a base part facing the base sheet gradually decreases toward an end portion.

9 Claims, 6 Drawing Sheets

(58) Field of Classification Search
CPC .............. A61M 2037/0053; A61L 31/10; A61L 31/14; A61L 2420/02
See application file for complete search history.

(56) References Cited

U.S. PATENT DOCUMENTS

| | | | |
|---|---|---|---|
| 9,974,936 | B2 | 5/2018 | Jung et al. |
| 10,245,423 | B2 | 4/2019 | Jung et al. |
| 2011/0237925 | A1 | 9/2011 | Yue et al. |
| 2012/0296280 | A1 | 11/2012 | Eum |
| 2014/0066864 | A1 | 3/2014 | Eum |
| 2016/0067469 | A1* | 3/2016 | Jung .............. C09D 101/08 264/129 |
| 2016/0129164 | A1 | 5/2016 | Lee et al. |

FOREIGN PATENT DOCUMENTS

| | | |
|---|---|---|
| JP | 2016-2194 A | 1/2016 |
| KR | 10-0572539 B1 | 4/2006 |
| KR | 10-0781702 B1 | 12/2007 |
| KR | 10-2012-0068516 A | 6/2012 |
| KR | 10-1180032 B1 | 9/2012 |
| KR | 10-1386442 B1 | 4/2014 |
| KR | 10-2014-0131879 A | 11/2014 |
| KR | 10-1488397 B1 | 2/2015 |
| KR | 10-1549086 A | 9/2015 |
| KR | 10-1590172 B1 | 1/2016 |
| WO | 2004/019777 A2 | 3/2004 |
| WO | 2011/093674 A2 | 8/2011 |

OTHER PUBLICATIONS

Written Opinion dated Nov. 15, 2017 by the International Searching Authority in counterpart International Patent Application No. PCT/KR2017/008591. (PCT/ISA/237).

Decision to Grant dated Dec. 5, 2017 by the Korean Intellectual Property Office in counterpart Korean Patent Application No. 10-2016-0142099.

* cited by examiner (a)

(b)

(a)

(b)

(c)

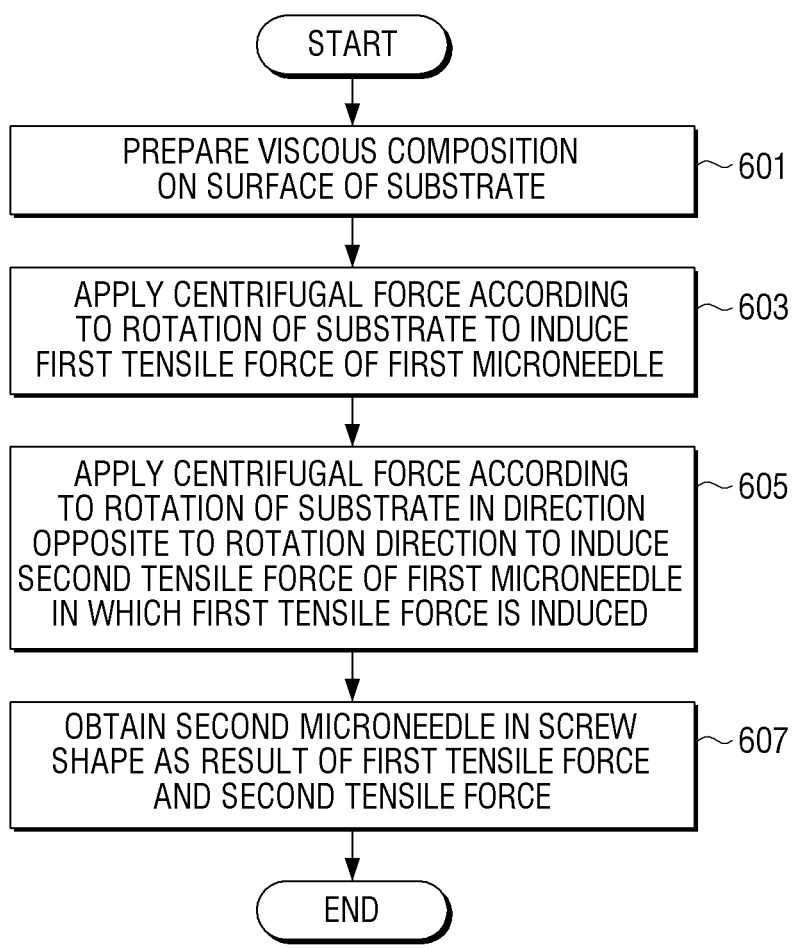

MICRONEEDLE PATCH, AND METHOD AND DEVICE FOR MANUFACTURING MICRONEEDLE

TECHNICAL FIELD

The disclosure relates to a method of manufacturing a microneedle and a microneedle patch including the microneedle manufactured therefrom. More particularly, the disclosure relates to a method of manufacturing a microneedle that is formed by application of a centrifugal force and a microneedle patch including the microneedle manufactured therefrom.

BACKGROUND ART

When a biological active substance is injected into the skin of a person, conventional injection needles may be used, which may cause pain of an injection site, damage bleeding of the skin, infectious diseases caused by injection needles, etc.

In this regard, recently, a method of delivering a biological active substance through the skin using a microneedle (or ultrafine needle) has been actively studied. Microneedles may have tens to hundreds of micro diameters to penetrate the stratum corneum of the skin, which is a major barrier layer.

Unlike conventional injection needles, the microneedle may be characterized by painless skin penetration and no trauma. Also, the microneedles must penetrate the stratum corneum of the skin, and thus some degree of physical hardness may be required. Also, an appropriate length may be required for the biological active substance to reach the epidermal layer or dermal layer of the skin.

Further, in order for the biological active substances of hundreds of microneedles to be effectively delivered into the skin, the skin permeability of the microneedles must be high and maintained for a certain period of time after being inserted into the skin and dissolving.

Recently, microneedle patches in the form of a patch having one surface on which the microneedles are arranged have been used. However, there is a problem that the microneedles are easily detached after attachment because the surface on which the microneedles are arranged has no adhesion.

A microneedle may be manufactured in a sharp shape to penetrate the skin.

For example, a microneedle may have a conical shape, a pyramid shape, or a bullet shape according to a manufacturing method or a general needle shape having a constant diameter from a base portion and a pointed end portion.

In this case, when the end portion is flat or is not uniformly pointed, it may be difficult for hundreds of microneedles to enter into the skin.

For example, when a microneedle patch on which microneedles having a conical shape, a pyramid shape, or a flat end portion are arranged is attached to the skin, the skin permeability of the microneedle reaching the epidermal layer or dermal layer below the stratum corneum of the skin may be within 50%. In particular, there a problem occurs even when a microneedle in a straight shape such as a conical shape, a pyramid shape, or a bullet shape is inserted into the skin, because there is no part to be caught, the microneedle may be easily removed after insertion.

Thus, a need to manufacture a microneedle that easily enters into the skin and is not well removed after entry is required.

In addition, it is to be understood that the technical problem of the disclosure is not limited to the above-mentioned technical problem, and other technical problems which are not mentioned are clearly understood from the following description to those skilled in the art.

SUMMARY

A microneedle patch of the disclosure may include an adhesive sheet to be adhered to the skin; and a base sheet on which microneedles are arranged, wherein a shape of the microneedles has a spirally twisted screw shape having a first inclination toward a first direction and a second inclination toward a second direction opposite to the first direction, and wherein a diameter of a base portion facing the base sheet gradually decreases toward an end portion.

A method of manufacturing a microneedle of the disclosure may include preparing a first microneedle on a surface of a substrate; applying a centrifugal force according to rotation of the substrate to induce a first tensile force of the first microneedle; applying a centrifugal force according to rotation of the substrate in a direction opposite to a rotation direction to induce a second tensile force of the first microneedle in which the first tensile force is induced; and obtaining a second microneedle in a screw shape as a result of the first tensile force and the second tensile force.

A device for manufacturing a microneedle of the disclosure may include a substrate configured to provide a surface on which a first microneedle is prepared; a motor configured to rotate the substrate such that a centrifugal force to induce a first tensile force of the first microneedle is applied, and rotate the substrate in a direction opposite to a rotation direction to apply a centrifugal force to induce a second tensile force of the first microneedle, and a rotary shaft configured to deliver a rotational force of the motor to the substrate.

According to the microneedle patch formed according to the manufacturing method of the disclosure, a microneedle easily enters into the skin and is not well removed even after entry, and thus an effective rate at which a viscous composition included in the microneedle is absorbed into the skin may be increased.

Further, when the microneedle is coated, the physical hardness of the microneedle is enhanced, and leakage of the viscous composition that may occur during entry into the skin may be minimized.

In addition, the effects obtainable or predicted from the embodiments of the disclosure will be directly or implicitly disclosed in the detailed description of the embodiments of the disclosure. For example, various effects to be predicted according to an embodiment of the disclosure will be disclosed within the detailed description to be described later.

DESCRIPTION OF DRAWINGS

FIG. 6 is a flowchart illustrating a method of manufacturing microneedles according to an embodiment of the disclosure.

DETAILED DESCRIPTION

Figure 1:
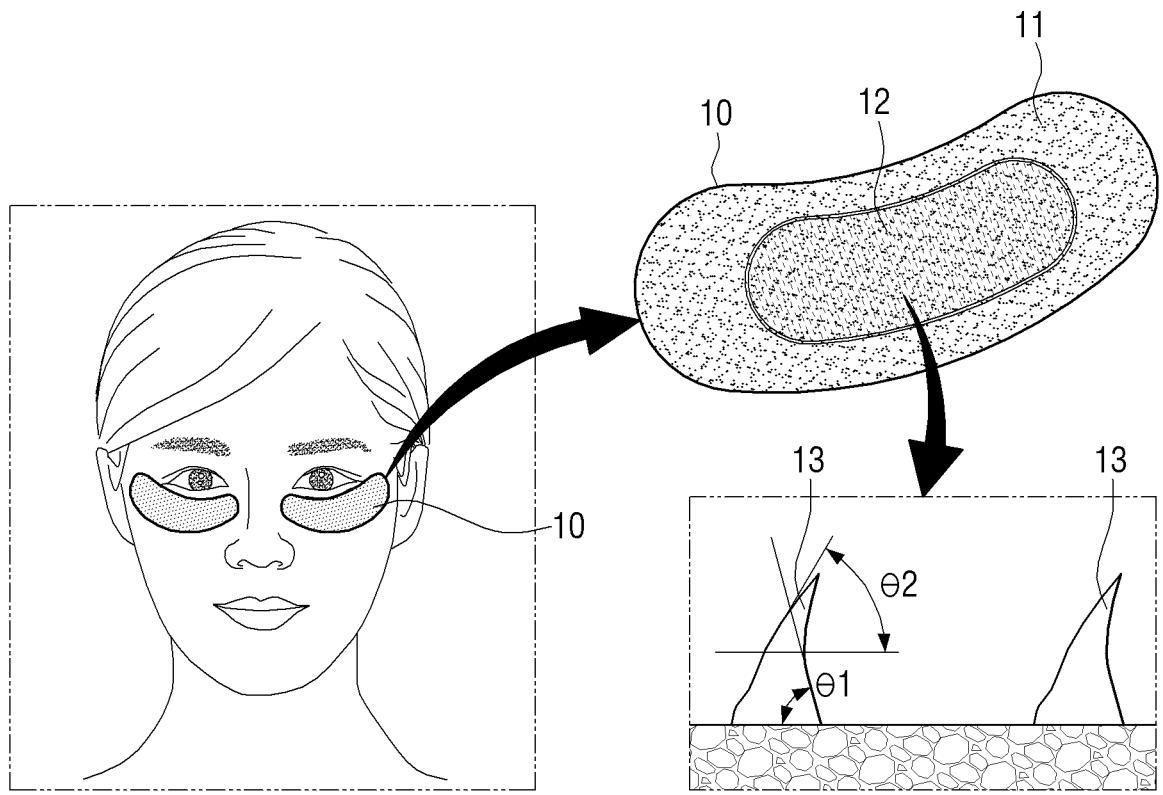
FIG. 1 shows a microneedle patch, according to an embodiment of the disclosure.

Various embodiments disclosed herein will be described with reference to accompanying drawings. However, it should be understood that the description disclosed in this specification is not limited to a specific embodiment and that modification, equivalent, and/or alternative on the various embodiments described herein are included in the contents of this specification. With regard to description of drawings, similar elements may be marked by similar reference numerals.

In various embodiments of the disclosure, the expressions "have", "may have", "include" and "comprise", or "may include" and "may include" used herein indicate existence of corresponding features (e.g., elements such as numeric values, functions, operations, or components) but do not exclude presence of additional features.

In various embodiments of the disclosure, the expressions "A or B", "at least one of A or/and B", "one or more of A or/and B", and the like may include all combinations of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms such as "first", "second", and the like used herein may refer to various elements regardless of the order and/or priority of the elements and may be used to distinguish an element from another element, not to limit the elements. For example, "a first user device" and "a second user device" may indicate different user devices regardless of the order or priority thereof. For example, without departing the scope of the disclosure, a first element may be referred to as a second element, and similarly, a second element may be referred to as a first element.

Terms used in this specification may be used to describe specific embodiments and may not be intended to limit other embodiments. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary, should also be interpreted as is customary in the relevant related art and not in an idealized or overly formal meaning unless expressly so defined herein in this specification. In some cases, even if terms are terms that are defined in the specification, they may not be interpreted to exclude embodiments of this specification.

In the disclosure, a viscous composition may mean a composition capable of forming a microneedle by changing its shape by the centrifugal force of a manufacturing device.

The viscosity of the composition may be controlled by the intrinsic viscosity of a viscous material, and may be variously changed depending on a type, concentration, or temperature of a substance included in the composition.

The viscous composition of the disclosure may be at least one of, for example, a complex polysaccharide composed of hyaluronic acid including amino acid and uronic acid and salts thereof, polyvinylpyrrolidone, cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, gum arabic, alginic acid, gelatin, gellan gum, carrageenan, karaya gum, curdlan, chitosan, chitin, tara gum, tamarind gum, tragacanth gum, furcelleran, pectin, pullulan, hydroxypropyl methyl cellulose, hydroxyalkyl cellulose, hydroxyethyl cellulose, hydroxypropyl cellulose, ethyl hydroxyethyl cellulose, alkyl cellulose and carboxymethyl cellulose and hydroxypropylmethyl cellulose, a combination of these, or a mixture of two or more selected from these. The viscous composition may include a biological active substance such as a biocompatible or biodegradable substance.

The biocompatible substance may mean a substance that is not toxic to humans, chemically inert, and has no immunogenicity. The biodegradable substance may mean a substance that may be decomposed by body fluids or microorganisms in a living body.

The biodegradable substance may include at least one of, for example, hyaluronic acid, sodium hyaluronate, lactos, DW-EGF (sh-Oligopeptid-1), polyester, polyhydroxyalkanoate (PHAs), poly($\alpha$-hydroxyacids), poly($\beta$-hydroxyacids), poly(3-hydrobutyrate-co-valerate; PHBV), poly(3-hydroxyproprionate; PHP), poly(3-hydroxy hekssano eight; PHH), poly(4-hydroxyacid), poly(4-hydroxybutyrate), poly (4-hydroxyvalerate), poly(4-hydroxyhexanoate), poly(ester amide), polycaprolactone, polylactide, polyglycolide, poly (lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazene, PHA-PEG, ethylene vinyl alcohol copolymer (EVOH), polyurethane, silicone, polyester, polyolefins, polyisobutylenes and ethylene-alpha olefin copolymers, styrene-isobutylene-styrene triblock copolymers, acrylate polymers and copolymers, vinyl halide polymers and copolymers, polyvinyl chloride, polyvinyl ether, polyvinyl methyl ether, polyvinylidene halide, polyvinylidene fluoride, polyvinylidene chloride, polyfluoroalkenes, polyperfluoroalkenes, polyacrylonitriles, polyvinyl ketones, polyvinyl aromatics, polystyrenes, polyvinyl esters, polyvinylacetates, ethylene-methyl methacrylate copolymers, acrylonitrile-styrene copolymers, ABS resin and ethylene-vinyl acetate copolymer, polyamide, alkyd resin, polyoxymethylene, polyimide, polyether, polyacrylate, polymethacrylate, polyacrylic-co-maleic acid, chitosan, dextran, cellulose, heparin, alginate, inulin, starch and glycogen, a combination of these, or a mixture of two or more selected from these.

According to an embodiment, the viscous composition may be dissolved in a suitable solvent to exhibit viscosity. Alternatively, the viscous composition may be fused by heat to exhibit viscosity. The solvent used to prepare the viscous composition may be at least one of water, anhydrous or water-containing lower alcohol having 1 to 4 carbon atoms, a combination of these, or a mixture of two or more selected from these.

According to an embodiment, the viscous composition may further include a drug. That is, drug of the biocompatible substance may be mixed in preparation of the viscous composition. The drug may include chemical drugs, protein drugs, peptide drugs, nucleic acid molecules for gene therapy, nano particles, etc. Also, the drug may include anti-inflammatory agents, analgesic agents, anti-arthritic agents, antispasmodic agents, antidepressant agents, antipsychotic agents, neurotransmitters, anti-anxiety agents, drug antagonists, antiparkins disease drugs, cholinergic agonists, anticancer drugs, antiangiogenic agents, immunosuppressive agents, antiviral agents, antibiotics, appetite suppressants, analgesics, anticholinergics, antihistamines, antimigraine agents, hormonal agents, coronary, cerebral or peripheral vasodilators, contraceptives, antithrombotic agents, diuretics, anti-hypertensive, cardiovascular therapeutic agents, cosmetic ingredients (e.g., an antiwrinkle agent, an aging inhibitor and a skin whitening agent), etc.

According to an embodiment, the viscous composition may include a protein drug, a peptide drug or a vitamin. The protein drug or the peptide drug may include, for example, a hormone, a hormone analogue, an enzyme, an enzyme inhibitor, a signal transduction protein or a portion thereof, an antibody or a portion thereof, a single chain antibody, a binding protein or its binding domain, antigens, adhesion proteins, structural proteins, regulatory proteins, toxin proteins, cytokines, transcription factors, blood coagulation factors and vaccines, and the like but is not limited thereto. More specifically, the protein/peptide drug may include at least one of insulin, insulin-like growth factor 1(IGF-1), growth hormone, erythropoietin, granulocyte-colony stimulating factors(G-CSFs), granulocyte/macrophage-colony stimulating factors(GM-CSFs), interferon alpha, interferon beta, interferon gamma, interleukin-1 alpha and beta, interleukin-3, interleukin-4, interleukin-6, interleukin-2, epidermal growth factors(EGFs), calcitonin, adrenocorticotropic hormone(ACTH), tumor necrosis factor(TNF), atobisban, buserelin, cetrorelix, deslorelin, desmopressin), dynorphin A(1-13), elcatonin, eleidosin, eptifibatide, growth hormone-releasing hormone-II(GHRH-II) gonadorelin, goserelin, histrelin, leuprorelin, lyphresin(lypressin, octreotide, oxytocin, pitressin, secretin, sincalide, terlipressin, thymopentin, thymosine, alpha 1, triptorelin, bivalirudin, carbetocin, cyclosporine, exedine, lanreotide, luteinizing hormone-releasing hormone (LHRH), nafarelin, parathyroid hormone, pramlintide, T-20(enfuvirtide), thymalfasin and chicotanide.

According to an embodiment, the viscous composition may include energy. In this case, a microneedle may be used to transmit or deliver energy such as heat energy, light energy, electric energy and the like. For example, in photodynamic therapy, the microneedle may be used to directly act light to tissues or to induce light to a specific part of the body such that light acts to a medium such as light-sensitive molecules.

FIG. 1 shows a microneedle patch 10, according to an embodiment of the disclosure.

Referring to FIG. 1, the microneedle patch 10 may include an adhesive sheet (or patch sheet) 11 to be adhered to the skin, a base sheet (or needle sheet) 12 on which microneedles 13 are arranged, and the microneedles 13 arranged on the base sheet 12.

The adhesive sheet 11 and the base sheet 12 may be formed of, for example, a non-conductive material and may have flexibility to allow the microneedles 13 to be adhered to the skin along the curvature of the skin.

Materials of the adhesive sheet 11 and the base sheet 12 may include at least one of, for example, a cellulose resin, a polyester resin such as polyethylene terephthalate (PET) and polyethylene naphthalate (PEN), a polyethylene resin, a polyvinyl chloride resin, polycarbonate (PC), polyethylene sulfone (PES), polyether ether ketone (PEEK), polyphenylene sulfide (PPS), and hydrocolloid or a combination of these.

The microneedles 13 may be formed of a viscous composition and arranged on the base sheet 12. The viscous composition may include a biocompatible or biodegradable substance. Examples of the viscous composition are defined above and a detailed description thereof is omitted.

The viscous composition may also be coated with other biodegradable substances. For example, the biodegradable substance to be coated may be a composition of a combination of oligo and heparonic acid.

The microneedles 13 may have a screw shape. A method of manufacturing the microneedles 13 having the screw shape will be described in detail later with reference to FIGS. 3 to 6.

A shape of the microneedles 13 may have a spirally twisted screw shape having a first inclination θ1 toward a first direction and a second inclination θ2 toward a second direction opposite to the first direction.

An inclination of the microneedles 13 means a degree to which the microneedles 13 are laid or inclined with respect to a surface of a substrate. Alternatively, the inclination of the microneedles 13 may mean a value of an inclination angle or a ratio between an oblique surface of the microneedles 13 and a horizontal plane or a plane parallel to the horizontal plane.

Also, a diameter of a base portion of the microneedles 13 facing the base sheet 12 may gradually decrease toward an end portion.

Figure 2:
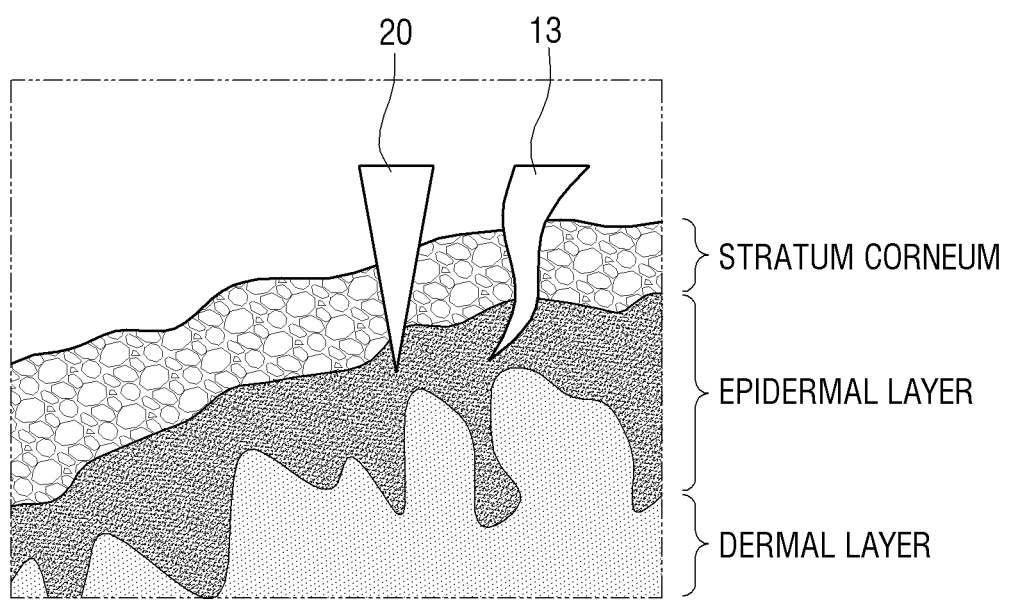
FIG. 2 is a cross-sectional view of microneedles inserted into the skin, according to an embodiment of the disclosure.
Figure 3:
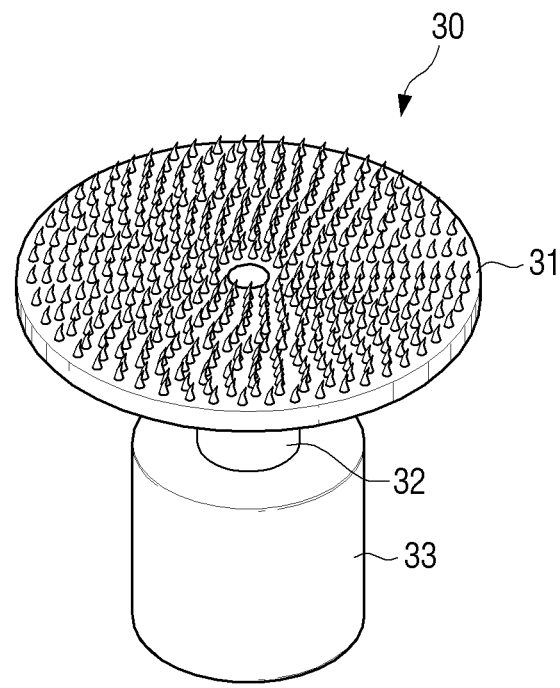
FIG. 3 shows a manufacturing device for manufacturing microneedles according to the disclosure.
Figure 3:
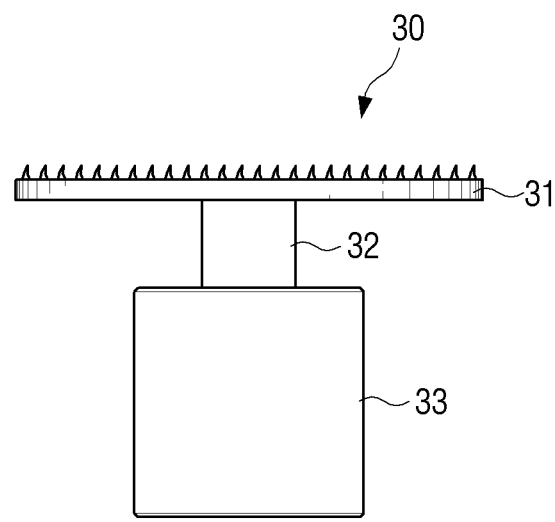

FIG. 2 is a cross-sectional view of the microneedles 13 inserted into the skin.

In FIG. 2, there may be a state in which the microneedle 13 of the disclosure and an existing microneedle 201 are inserted into the skin.

At this time, a height of the microneedle 13 may be appropriately selected to reach an epidermal layer or a dermal layer below a stratum corneum.

For example, the human skin may include the stratum corneum (<20 μm), the epidermal layer (<100 μm) and the dermal layer (300 μm-2,500 μm) from the epidermis. Therefore, in order to deliver a viscous composition containing a skin cosmetic ingredient or drug without pain to a specific skin layer, a diameter of an end portion of the microneedle 13 may be within 30 μm, and the height of the microneedle 13 may be between 50 μm and 500 μm to reach the epidermal layer or the dermal layer below the stratum corneum.

In FIG. 2, the existing microneedle 20 in a conical shape has a structure in which the existing microneedle 20 is easily removed after being inserted. On the other hand, the microneedle 13 of the disclosure in a screw shape has a structure in which the microneedle 13 is difficult to separate when inserted once. In this case, the microneedle 13 is kept in the skin for a certain period of time such that the viscous composition contained in the microneedle 13 may be sufficiently absorbed into the skin.

FIGS. 3(a) and 3(b) show a manufacturing device 30 for manufacturing the microneedles 13 according to the disclosure.

FIG. 3(a) is a perspective view of the manufacturing device 30, and FIG. 3(b) is a front view of the manufacturing device 30.

The manufacturing device 30 may be, for example, a centrifugal separator or a part of the centrifugal separator.

The manufacturing device 30 may include the substrate 31 on which the microneedles 13 containing a viscous composition are prepared, a rotary shaft 32 for transmitting a rotational force of a motor 33 to the substrate 31, and the motor 33 for providing the rotational force to the rotary shaft 32. According to various embodiments, the manufacturing device 30 may further include a housing (not shown) surrounding the outside of the configurations. When the housing (not shown) is added, the stability of the manufacturing device 30 may be increased and an external disturbance factor that may be involved in manufacturing the microneedles 13 may be blocked.

The substrate 31 may be formed of a material such as polymers, organic chemicals, metals, ceramics, semiconductors, etc. but is not limited to the examples described above. The substrate 31 may be provided integrally with the rotary shaft 32, or may be provided in a form capable of being combined and separated.

As shown in FIGS. 3(a) and 3(b), when the rotary shaft 32 is positioned at the center of the substrate 31, the substrate 31 may rotate clockwise or counterclockwise in accordance with a rotation of the rotary shaft 32 according to the transmission of the rotary force of the motor 33.

The motor 33 may adjust at least one of a rotation direction, a rotation speed, a rotation acceleration and a rotation time of the substrate 31.

According to various embodiments, when a viscous composition is prepared on the surface of the substrate 31, the motor 33 may rotate the substrate 31 to apply a centrifugal force to induce a first tensile force of the viscous composition to form a first microneedle, and rotate the substrate 31 again to apply the centrifugal force to induce a second tensile force of the viscous composition.

According to various embodiments, the first microneedle formed from the viscous composition may be prepared on the surface of the substrate 31. In this case, the preparation of the first microneedle on the substrate 31 may include a state in which the manufacturing device 30 applies the centrifugal force to the viscous composition such that the first microneedle is formed on the surface of the substrate 31 as described above.

In this case, in order to form the second microneedle, the motor 33 may rotate the substrate 31 to apply the centrifugal force to induce the first tensile force of the viscous composition, and rotate the substrate 31 again to apply the centrifugal force to induce the second tensile force of the viscous composition.

According to various embodiments, the manufacturing device 30 may further include at least one of a preparation device (not shown) for preparing a microneedle or a viscous composition and an obtaining device (not shown) for obtaining the microneedle manufactured according to a manufacturing process of the disclosure.

FIGS. 4(a), 4(b), and 4(c) show a manufacturing process of the microneedles 13 in a screw shape according to an embodiment of the disclosure.

First, as shown in FIG. 4(a), a first microneedle 40 may be prepared on a surface of the substrate 31 of the manufacturing device 30.

The first microneedle 40 prepared on the surface of the substrate 31 may have a straight shape such as a conical shape, a pyramidal shape, or a bullet shape, and may be a microneedle before solidifying.

A process of preparing the first microneedle 40 on the substrate 31 may be performed through a separate preparation device or directly by a manufacturer.

Alternatively, the process of preparing the first microneedle 40 on the substrate 31 may include a state in which the manufacturing device 30 applies a centrifugal force to a viscous composition to form the first microneedle 40 on the surface of the substrate 31.

Next, as shown in FIG. 4(b), a rotation of the substrate 31 in one direction may induce a tensile force of the first microneedle 40 located on the surface of the substrate 31.

When the centrifugal force is applied by the rotation of the substrate 31, a first tensile force may be induced in the first microneedle 40 such that an intermediate composition 41 having a first inclination in a direction opposite to a rotation direction of the substrate 31 is formed.

The direction in which the substrate 31 rotates may be clockwise or counterclockwise.

The application of the centrifugal force may mean that, for example, the substrate 31 on which the first microneedle 40 is prepared rotates such that the first microneedle 40 is in a state of receiving inertia in the direction opposite to the rotation direction. Accordingly, the first microneedle 40 may be bent in the direction opposite to the rotation direction.

The first microneedle 40 may be located close to the center of the substrate 31 or away from the center of the substrate 31. As the first microneedle 40 is located farther away from the center of the substrate 31 (i.e., as the diameter increases with respect to the center of the substrate 31), the intermediate composition 41 may have a shape in which a first inclination gradually increases. On the other hand, as the first microneedle 40 is located farther away from the center of the substrate 31 (i.e., as the diameter increases with respect to the center of the substrate 31), the intermediate composition 41 have a shape in which the first inclination gradually decreases.

Also, a shape, a diameter, a height and an aspect ratio of the intermediate composition 41 may be adjusted according to at least one of the rotation direction, a rotation speed, a rotation acceleration and a rotation time of the substrate 31 under the control of the manufacturing device 30. Here, the height of the intermediate composition 41 may mean a vertical length from an end portion of the intermediate composition 41 to a base portion of the intermediate composition 41 facing the substrate 31. The end portion may mean a part of the intermediate composition 41 having a minimum diameter. Further, the diameter may mean a diameter of one end face of the intermediate composition 41. Further, the aspect ratio may mean a ratio of the height and the diameter of the intermediate composition 41.

When the centrifugal force is applied to the substrate 31, as the centrifugal force is increased, the diameter of the base portion of the intermediate composition 41 may be reduced, and the length and the aspect ratio thereof may be increased. Further, as the centrifugal force decreases, the diameter of the base portion of the intermediate composition 41 may be increased, and the length and the aspect ratio thereof may be reduced. In other words, as the rotation speed of the substrate 31 increases, the diameter of the base portion of the intermediate composition 41 may be reduced, and the length and the aspect ratio thereof may be increased. Further, as the rotation speed of the substrate 31 decreases, the diameter of the base portion of the intermediate composition 41 may be increased, and the length and the aspect ratio may be reduced.

Further, as a time during which the centrifugal force is applied to the substrate 31 increases, the diameter of the base portion of the intermediate composition 41 may be reduced, and the length and the aspect ratio thereof may be increased. Further, as the time during which the centrifugal force is applied to the substrate 31 decreases, the diameter of the base portion of the intermediate composition 41 may be increased r, and the length and the aspect ratio thereof may be reduced.

As a manufacturing process in FIG. 4(b), the rotation direction of the substrate 31 may be clockwise, the rotation speed per minute (rpm) of the substrate 31 may have a value between 1,000 rpm and 4000 rpm, and the rotation time of the substrate 31 may have a value between 30 seconds and 180 seconds, but the manufacturing process is not limited to the above example.

Next, as shown in FIG. 4(c), according to the rotation of the substrate 31 in the direction opposite to the rotation direction in FIG. 4(b), the tensile force of the intermediate composition 41 located on the surface of the substrate 31 may be induced.

When the centrifugal force is applied according to the rotation of the substrate 31, a second tensile force may be induced in the intermediate composition 41 formed through the process of FIG. 4(b) such that the second microneedle 13 may be formed having a second inclination in the direction opposite to the rotation direction of the substrate 31. Then, the second microneedle 13 may be hardened such that the second microneedle 13 having a screw shape may be manufactured.

The direction in which the substrate 31 rotates may be counterclockwise or clockwise. The direction in which the substrate 31 rotates may be opposite to the rotation direction of the substrate 31 in FIG. 4(b). For example, when the substrate 31 rotates clockwise in FIG. 4(b), the rotation direction of the substrate 31 in FIG. 4(c) may be counterclockwise. For another example, when the substrate 31 rotates counterclockwise in FIG. 4(b), the rotation direction of the substrate 31 in FIG. 4(c) may be clockwise.

In this case, according to at least one of the position or an amount of the intermediate composition 41, the rotation direction, the rotation speed, the rotation acceleration and the rotation time of the substrate 31 according to the control of the manufacturing device 30, the shape, the diameter, the height, and the aspect ratio, and the like of the second microneedle 13 may be adjusted. An example of a modification of the intermediate composition 41 corresponds to an example of a modification of the first microneedle 40 of FIG. 4(b), and thus a redundant description thereof is omitted.

As a manufacturing process in FIG. 4(c), the rotation direction of the substrate 31 is counterclockwise, the rotation speed per minute (rpm) of the substrate 31 may have a value between 1,000 rpm and 4,000 rpm, and the rotation time of the substrate 31 may have a value between 30 seconds and 180 seconds, but the manufacturing process is not limited to the above example.

When the second microneedles 13 in the screw shape having the first tensile force and the second tensile force are formed through the manufacturing process of FIGS. 4(a) to 4(c), a process of solidifying the generated second microneedles 13 may be performed by using a physical or chemical method. The process of solidifying the second microneedles 13 may proceed with a process of rotating the first microneedle 40 or the intermediate composition 41 in step of FIG. 4(b) or 4(c) described above or may proceed after the second microneedles 13 in the screw shape are formed. Alternatively, the solidifying process may be partially performed in the step of FIG. 4(b), and the solidifying process may be further performed in the step of FIG. 4(c).

Next, the hardened second microneedles 13 in the screw shape may be obtained.

For example, the second microneedles 13 may be dissolved, burned, or physically removed using an appropriate organic solvent. The second microneedles 13 may be removed using the appropriate organic solvent. Alternatively, the second microneedles 13 may be sucked and removed.

Alternatively, when the second microneedles 13 are provided on a tape, the second microneedles 13 may be extracted with the tape and attached to a base sheet of a microneedle patch. In this case, in consideration of an area of the base sheet, the second microneedles 13 may be punched or extracted together with the second microneedles 13 of the tape on which the second microneedles 13 are provided and attached to the base sheet.

A process of obtaining the microneedles 13 may be performed through a separate obtaining device (not shown) or may be performed directly by a manufacturer.

Figure 5:
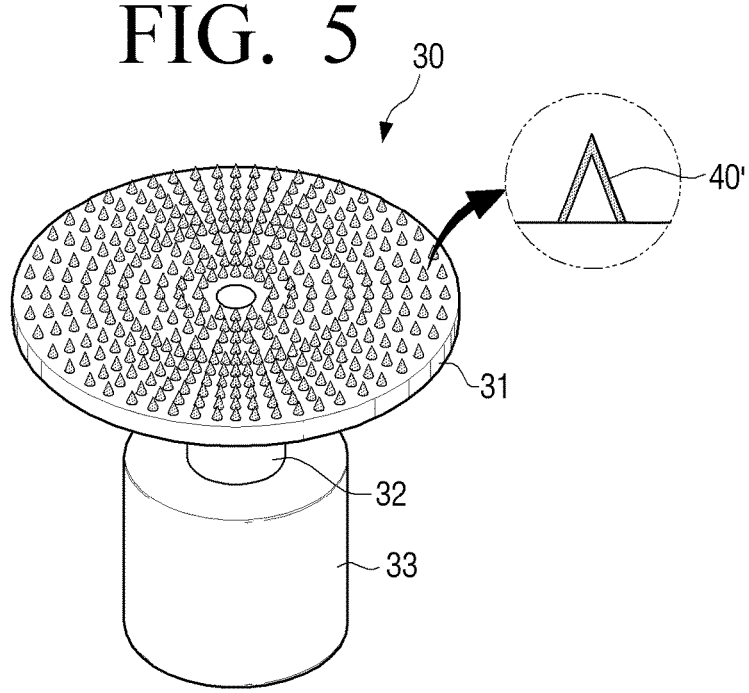
FIG. 5 is diagrams showing a process of manufacturing microneedles according to another embodiment of the disclosure.
Figure 5:
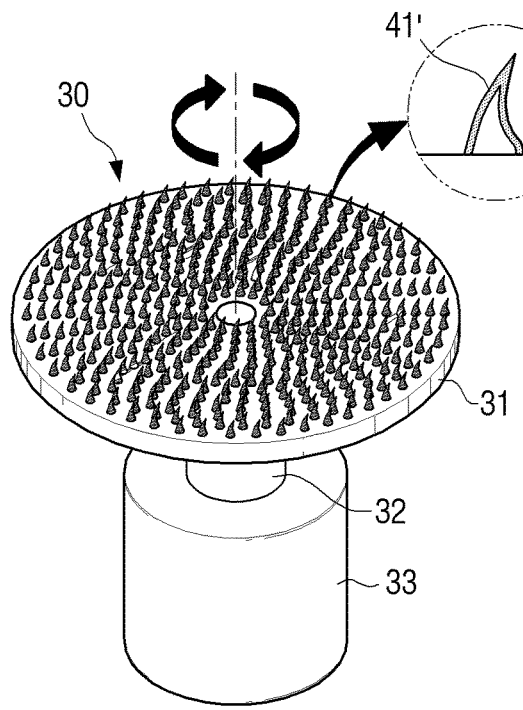
Figure 5:
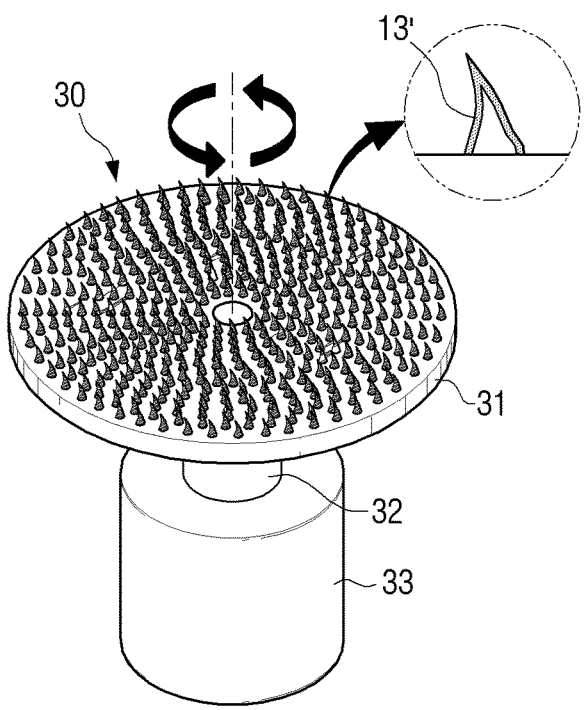

FIG. 5 is a diagram showing a process of manufacturing microneedles 13' according to another embodiment of the disclosure.

In FIG. 5(a), a coated first microneedle 40' may be prepared on a surface of the substrate 31 of the manufacturing device 30.

In this case, the coated first microneedle 40' may be a composition formed by coating a film with a biodegradable substance.

For example, when a material of the first microneedle 40' is a polymeric hyaluronic acid (for example, a molecular weight of 300K or more) which is a biodegradable substance, a coating material may be a low molecular weight hyaluronic acid (for example, a molecular weight of 10K or less). Further, when the material of the first microneedle 40' is the polymeric hyaluronic acid, oligo hyaluronic acid, which is a composition in which oligo and hyaluronic acid are mixed may be used as the coating material.

A hardness of the coated first microneedle 40' may be reinforced and easy to insert into the skin. Also, in the case of oligo hyaluronic acid mixed with oligo, a skin absorption power may be faster than that of the polymer hyaluronic acid. Accordingly, oligo hyaluronic acid may proceed to skin dissolution faster than polymer hyaluronic acid. That is, the skin dissolution of the oligo hyaluronic acid may first proceed during or after the insertion of a microneedle within a certain period, and then the skin dissolution of the polymer hyaluronic acid, which has better biological activity, may proceed continuously.

In this case, the dissolution of the polymer hyaluronic acid may be inhibited until entering the epidermal layer or the dermal layer in the skin, and thus the absorption power of the polymer hyaluronic acid in the epidermal layer or the dermal layer may increase.

On the other hand, the coated first microneedle 40' may be prepared on the substrate 31. A process of preparing the coated first microneedle 40' on the substrate 31 corresponds to a process of preparing the first microneedle 40 on the substrate 31 in FIG. 4(a), and thus a detailed description thereof is omitted.

Next, as shown in FIG. 5(b), according to the rotation of the substrate 31 in one direction, a tensile force of the coated first microneedle 40' located on the surface of the substrate 31 may be induced.

When a centrifugal force is applied as the substrate 31 rotates, a first tensile force may be induced in the coated first microneedle 40' to form a coated intermediate composition 41' having a first inclination in a direction opposite to a rotation direction of the substrate 31.

Figure 4:
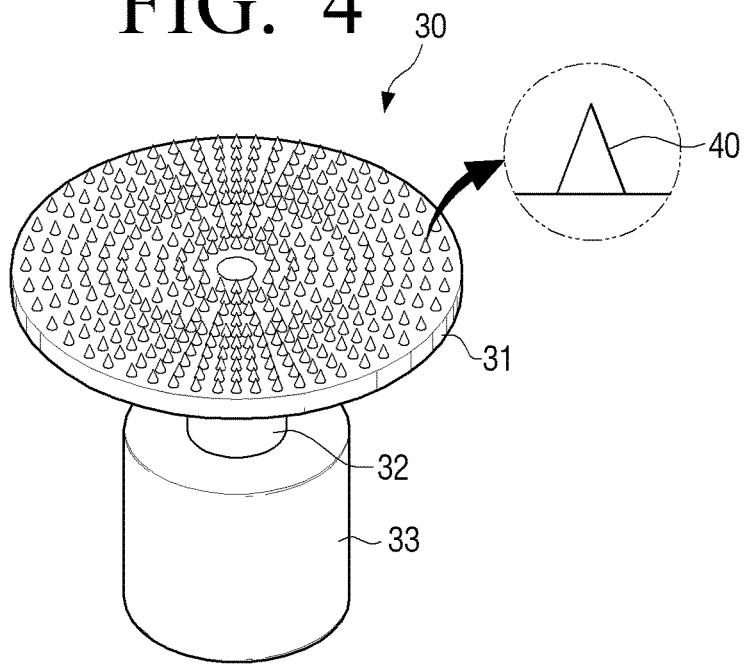
FIG. 4 shows a manufacturing process of microneedles in a screw shape according to an embodiment of the disclosure.
Figure 4:
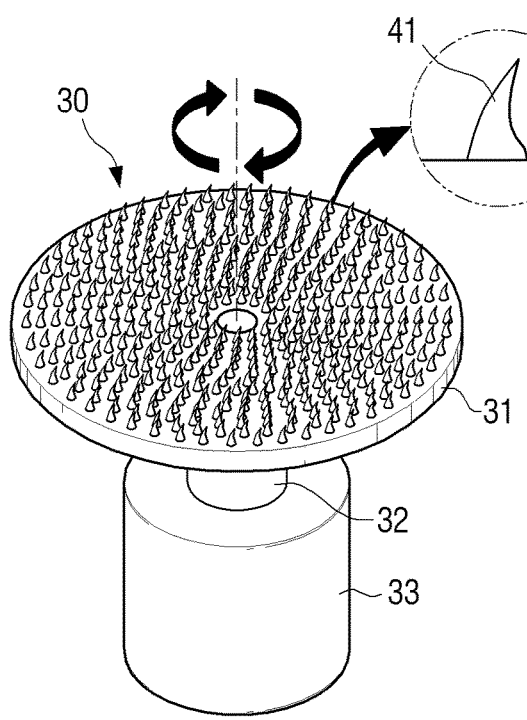
Figure 4:
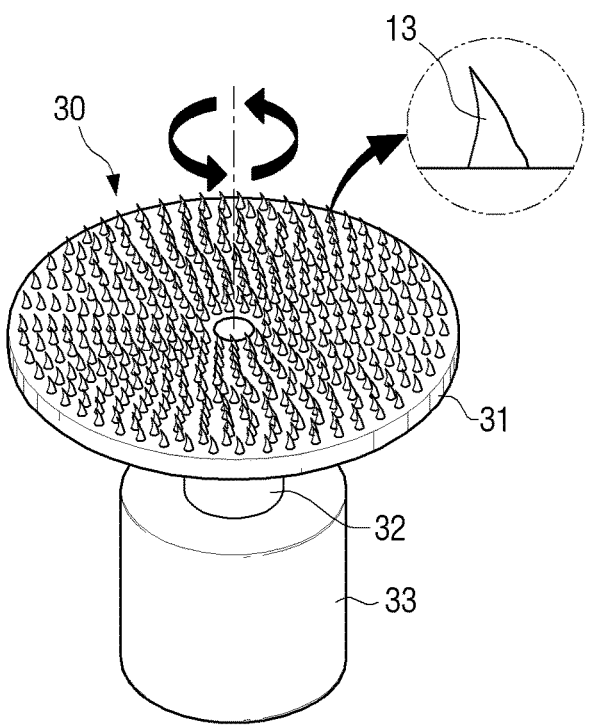

In this case, the hardness of the first microneedles 40' may be reinforced because of the coated film, and thus a degree to which the coated first microneedle 40' is stretched may be relatively small as compared with FIG. 4(c). That is, when the centrifugal force is applied to the coated first microneedle 40', a diameter of a base portion of the coated intermediate composition 41' may be increased, and a length and an aspect ratio thereof may be reduced. On the other hand, when the centrifugal force is applied to the first microneedle 40 of FIG. 4 which is not coated, the diameter of the base portion of the intermediate composition 41 may be reduced, and the length and aspect ratio thereof may be increased.

On the other hand, according to at least one of the position or an amount of the coated first microneedle 40', the rotation direction, the rotation speed, the rotation acceleration and the rotation time of the substrate 31 according to the control of the manufacturing device 30, the shape, the diameter, the height, and the aspect ratio, and the like of the coated intermediate composition 41' may be adjusted. An example of a modification of the coated first microneedle 40' corresponds to an example of a modification of the intermediate composition 41 of FIG. 4(*b*), and thus a redundant description thereof is omitted.

As a manufacturing process in FIG. 5(*b*), the rotation direction of the substrate 31 is counterclockwise, the rotation speed per minute (rpm) of the substrate 31 may have a value between 1,000 rpm and 4,000 rpm, and the rotation time of the substrate 31 may have a value between 30 seconds and 180 seconds, but the manufacturing process is not limited to the above example.

Next, as shown in FIG. 5(*c*), the coated intermediate composition 41' located on the surface of the substrate 31 may be induced according to the rotation of the substrate 31 in the direction opposite to the rotation direction in FIG. 5(*b*).

When the centrifugal force is applied as the substrate 31 rotates, a second tensile force may be induced in the coated intermediate composition 41' formed through the process of FIG. 5(*b*) to form a coated second microneedle 13' having a second inclination in the direction opposite to the rotation direction of the substrate 31. Then, the coated second microneedle 13' may be hardened such that the coated second microneedle 13' having a screw shape may be manufactured.

The direction in which the substrate 31 rotates may be counterclockwise or clockwise. The direction in which the substrate 31 rotates may be opposite to the rotation direction of the substrate 31 in FIG. 5(*b*).

In this case, according to at least one of the position or an amount of the coated intermediate composition 41', the rotation direction, the rotation speed, the rotation acceleration and the rotation time of the substrate 31 according to the control of the manufacturing device 30, the shape, the diameter, the height, and the aspect ratio, and the like of the coated second microneedle 13' may be adjusted. An example of a modification of the coated intermediate composition 41' corresponds to an example of a modification of the intermediate composition 41 of FIG. 4(*c*), and thus a redundant description thereof is omitted.

As a manufacturing process in FIG. 5(*c*), the rotation direction of the substrate 31 is counterclockwise, the rotation speed per minute (rpm) of the substrate 31 may have a value between 1,000 rpm and 4,000 rpm, and the rotation time of the substrate 31 may have a value between 30 seconds and 180 seconds, but the manufacturing process is not limited to the above example.

When the coated second microneedle 13' in the screw shape having the induced first tensile force and second tensile force are formed through the manufacturing process of FIGS. 5(*a*) to 5(*c*), a process of solidifying the generated coated second microneedle 13' may be performed by using a physical or chemical method.

Next, the hardened second microneedle 13' in the screw shape may be obtained. A method of obtaining the second microneedle 13' corresponds to a method of obtaining the second microneedle 13 of FIG. 4 described above, and thus a redundant description thereof is omitted.

As described above, in case of using the coated second microneedle 13' in the screw shape according to the disclosure, the hardness of the second microneedles 13' may be reinforced to facilitate entry into the skin, and also minimize leakage of a biodegradable substance (e.g., polymeric hyaluronic acid) during the entry into the skin. Also, because of the screw shape, the second microneedle 13' may not be removed from the inside of the skin, and thus the continuous inflow and absorption of the biodegradable substance may be increased.

According to various embodiments, the second microneedles may be plated.

That is, a film may be formed on the second microneedle in order to further increase the strength of the second microneedle. In this case, an outer diameter and hardness of the second microneedle may be adjusted by adjusting a plating thickness. Examples of a plating material used for plating treatment may include nickel, stainless steel, aluminum, chromium, cobalt based alloys, titanium, and alloys thereof, but are not limited thereto and any biologically applicable metal known in the art may be used.

In this case, a process of cutting an end portion of the second microneedle may be further included to form a pore for discharging a biodegradable substance or a biocompatible substance.

The process of cutting the end portion may be performed immediately after the second microneedle in the screw shape is formed, or may be performed on a hardened second microneedle.

According to various embodiments, the first and second microneedles may be injected with additional drug or cosmetic ingredients. The injection of additional ingredients may be performed during the above-described manufacturing process, or after the second microneedle in the screw shape is formed, or may be performed on a hardened second microneedle. Alternatively, additional ingredients may be injected through the pore generated by the cutting of the end portion after the second microneedle is plated.

FIG. 6 is a flowchart illustrating a method of manufacturing microneedles according to an embodiment of the disclosure.

First, in step 601, a preparation device or a manufacturer may prepare a first microneedle including a viscous composition on a surface of a substrate.

According to various embodiments, the first microneedle may be coated with a biodegradable substance. In this case, the biodegradable substance may be a composition in which oligo and hyaluronic acid are mixed.

Next, in step 603, a manufacturing device may apply a centrifugal force according to a rotation of the substrate to induce a first tensile force of the first microneedle.

Next, in step 605, the manufacturing device may apply the centrifugal force according to a rotation of the substrate in a direction opposite to a rotation direction to induce a second tensile force of the first microneedle in which the first tensile force is induced Next, in step 607, an obtaining device or the manufacturer may obtain a second microneedle in a screw shape formed as a result of the first tensile force and the second tensile force.

According to various embodiments, the second microneedle may have a spirally twisted screw shape to have a first inclination toward a first direction and a second inclination toward a second direction opposite to the first direction, and have a diameter of a base portion having a shape gradually decreasing toward an end portion.

Also, as the first microneedle located on the surface of the substrate is away from the center of the substrate, the first inclination and the second inclination of the second microneedle increase, and as the first microneedle located on the surface of the substrate is closer toward the center of the substrate, the first inclination and the second inclination of the second microneedle may decrease.

Also, as the centrifugal force of the substrate increases, a diameter of the base portion of the second microneedle may be reduced, and a length and an aspect ratio of the second microneedle may be increased, and as the centrifugal force of the substrate decreases, the diameter of the base portion of the second microneedle may be increased, and the length and the aspect ratio of the second microneedle may be reduced.

According to various embodiments, the above-described manufacturing method may further include at least one of a step of hardening the second microneedle and a step of plating the second microneedle.

At least a part of the manufacturing device (e.g., modules or functions thereof) or method (e.g., operations) of the disclosure according to an embodiment may be implemented as instructions stored in non-transitory computer readable recording media in the form of a program module. When the instructions are executed by a processor, the processor may perform a function corresponding to the instructions.

Here, the program may be stored in non-transitory computer readable recording media, read and executed by a computer, and thus the embodiments of the disclosure may be implemented.

Here, the non-transitory computer readable recording media refer to media that semi-permanently store data and are capable of being read by a device as well as include volatile or nonvolatile memory temporarily storing data for calculation or transmission such as registers, caches, buffers, etc. On the other hand, temporal transmission media such as signals, currents, etc., do not correspond to the non-transitory computer readable recording media.

Specifically, the above-described programs may be stored in and provided by the non-transitory computer readable recording media such as a CD, a DVD, a hard disk, a Blu-ray disk, a USB, an internal memory, a memory card, a ROM or a RAM and the like.

The above-described programs may also be stored in a memory of a server and transmitted for sale to a terminal (e.g., a device of the disclosure) that is connected with the server over a network, or transferred or registered to the server by a program provider (e.g., a program developer or a program manufacturing company). Also, when the above-described programs are sold to the terminal in the server, at least some of the programs may be temporarily created in a buffer of the server for transmission. In this case, the buffer of the server may be a non-transitory computer readable recording medium of the disclosure.

According to an embodiment, the non-transitory computer readable recording medium may store a program to cause the manufacturing device to perform preparing a first microneedle on a surface of a substrate, applying a centrifugal force in accordance with rotation of the substrate to induce a first tensile force of the first microneedle, applying the centrifugal force in accordance with rotation of the substrate in a direction opposite to a rotation direction to induce a second tensile force of the first microneedle in which the first tensile force is induced, and obtaining a second microneedle in a screw shape formed as a result of the first tensile force and the second tensile force.

It may be understood that the foregoing description of the disclosure is for the purpose of illustration and that those skilled in the art will readily understand that various changes in form and details may be made therein without departing from the spirit and scope of the disclosure. It is therefore to be understood that the embodiments described above are illustrative in all aspects and not restrictive. For example, each component described as a single entity may be distributed and implemented, and components described as being distributed may also be implemented in a combined form.

The scope of the disclosure is defined by the appended claims rather than the foregoing detailed description, and all changes or modifications that come within the meaning and range of the claims, and equivalent concept thereof, should be construed as being included within the scope of the disclosure.

The invention claimed is:

1. A method of manufacturing a microneedle, the method comprising:
    preparing the microneedle on a surface of a substrate;
    applying a centrifugal force according to rotation of the substrate to induce a first tensile force of the microneedle, to change a shape of the microneedle; and
    applying a centrifugal force according to rotation of the substrate in a direction opposite to a rotation direction to induce a second tensile force of the microneedle in which the first tensile force is induced, to further change the shape of the microneedle to a spirally twisted screw shape having a first inclination toward a first direction and a second inclination toward a second direction opposite to the first direction as a result of the first tensile force and the second tensile force.

2. The method as claimed in claim 1, wherein a diameter of a base portion of the microneedle having the spirally twisted screw shape gradually decreases toward an end portion.

3. The method as claimed in claim 2, wherein as the centrifugal force increases, the diameter of the base portion of the microneedle is reduced, and a length and an aspect ratio of the microneedle are increased, and
    wherein as the centrifugal force decreases, the diameter of the base portion of the microneedle is increased, and the length and the aspect ratio of the microneedle are reduced.

4. The method as claimed in claim 1, wherein the first inclination and the second inclination of the microneedle increase as the microneedle located on the surface of the substrate is away from a center of the substrate, and
    wherein the first inclination and the second inclination of the microneedle decrease as the microneedle located on the surface of the substrate is closer to the center of the substrate.

5. The method as claimed in claim 1, wherein a direction in which the substrate rotates is clockwise or counterclockwise.

6. The method as claimed in claim 1, wherein the preparing of the microneedle comprises preparing the microneedle in a straight shape on the surface of the substrate to be positioned, and
    wherein the straight shape is a cone shape, a pyramid shape, or a bullet shape.

7. The method as claimed in claim 1, wherein the microneedle is coated with a biodegradable substance.

8. The method as claimed in claim 7, wherein the biodegradable substance is a composition in which oligo and hyaluronic acid are mixed.

9. The method as claimed in claim 1, further comprising hardening the microneedle.

* * * * *